(12) United States Patent
Vuillemot

(10) Patent No.: US 9,717,573 B2
(45) Date of Patent: Aug. 1, 2017

(54) IN-SITU DENTAL RESTORATION PROCESS AND APPARATUS

(71) Applicant: William C. Vuillemot, DeWitt, MI (US)

(72) Inventor: William C. Vuillemot, DeWitt, MI (US)

(73) Assignee: William C. Vuillemot, DeWitt, MI (US)

( * ) Notice: Subject to any disclaimer, the term of this patent is extended or adjusted under 35 U.S.C. 154(b) by 736 days.

(21) Appl. No.: 14/086,249

(22) Filed: Nov. 21, 2013

(65) Prior Publication Data

US 2015/0140517 A1    May 21, 2015

(51) Int. Cl.
*A61C 13/00* (2006.01)
*A61C 9/00* (2006.01)

(52) U.S. Cl.
CPC ........ *A61C 13/0004* (2013.01); *A61C 9/0053* (2013.01); *A61C 13/0019* (2013.01); *A61C 13/0013* (2013.01)

(58) Field of Classification Search
CPC . A61C 13/00; A61C 13/0001; A61C 13/0003; A61C 13/0004; A61C 13/0006; A61C 9/0053; A61C 13/0013; A61C 13/0019
USPC .................................................... 700/97–98
See application file for complete search history.

(56) References Cited

U.S. PATENT DOCUMENTS

| | | | | |
|---|---|---|---|---|
| 3,987,545 A * | 10/1976 | Kennedy | ................ | A61C 13/00 433/223 |
| 4,368,040 A * | 1/1983 | Weissman | ............ | A61C 9/0006 433/223 |
| 5,224,049 A * | 6/1993 | Mushabac | .......... | G05B 19/4207 264/222 |
| 6,261,098 B1 * | 7/2001 | Persson | ................... | A61C 9/002 433/213 |
| 6,299,449 B1 * | 10/2001 | Carlson | ................... | A61C 13/26 433/180 |
| 6,488,638 B2 * | 12/2002 | Mushabac | .......... | A61C 13/0004 433/215 |
| 7,217,131 B2 | 5/2007 | Vuillemot | | |
| 7,536,234 B2 * | 5/2009 | Kopelman | ......... | A61C 13/0004 433/223 |
| 8,366,445 B2 | 2/2013 | Vuillemot | | |
| 8,623,026 B2 * | 1/2014 | Wong | ................. | A61B 17/1703 29/592 |
| 8,696,356 B2 * | 4/2014 | Hegyi | ...................... | A61C 5/04 433/215 |

(Continued)

*Primary Examiner* — Cris L Rodriguez
*Assistant Examiner* — Hao D Mai
(74) *Attorney, Agent, or Firm* — Butzel Long

(57) ABSTRACT

A dental restoration method that eliminates time-consuming, labor-intensive steps conventionally needed to fabricate molds, and thereby facilitates dental restorations in a shorter time, while reducing the discomfort and embarrassment sometimes associated with provisional restorations involves scanning an existing dental structure to generate a three-dimensional digital model of the existing dental structure, generating a three-dimensional digital model corresponding with a planned dental structure, and using an additive manufacturing process and apparatus (e.g., a 3-D printer) to fabricate the planned dental structure directly on the existing dental structure.

13 Claims, 3 Drawing Sheets

(56) References Cited

U.S. PATENT DOCUMENTS

| | | | | |
|---|---|---|---|---|
| 8,702,716 | B1* | 4/2014 | Stein | A61F 2/44 606/94 |
| 8,813,364 | B2* | 8/2014 | Schechner | A61C 13/0004 264/16 |
| 8,867,800 | B2* | 10/2014 | Bullis | A61C 13/0004 382/128 |
| 2002/0006217 | A1* | 1/2002 | Rubbert | A61C 7/00 382/131 |
| 2002/0015934 | A1* | 2/2002 | Rubbert | A61C 7/00 433/29 |
| 2004/0152051 | A1* | 8/2004 | Craig | A61C 19/066 433/215 |
| 2006/0003284 | A1* | 1/2006 | Sale | A61C 19/066 433/29 |
| 2006/0008777 | A1* | 1/2006 | Peterson | A61C 13/0019 433/223 |
| 2006/0063979 | A1* | 3/2006 | Rosenblood | A61B 1/0669 600/237 |
| 2007/0118243 | A1* | 5/2007 | Schroeder | A61B 17/8061 700/118 |
| 2008/0044796 | A1* | 2/2008 | Hsu | A61C 5/14 433/215 |
| 2009/0130449 | A1* | 5/2009 | El-Siblani | A61C 13/0013 428/409 |
| 2009/0222014 | A1* | 9/2009 | Bojarski | A61B 17/17 606/88 |
| 2010/0332248 | A1* | 12/2010 | Pettersson | G06F 19/321 705/2 |
| 2011/0086328 | A1* | 4/2011 | Wedeking | A61C 8/00 433/174 |
| 2011/0171604 | A1* | 7/2011 | Durbin | A61C 5/08 433/213 |
| 2015/0216732 | A1* | 8/2015 | Hartwell | A61F 13/00021 604/319 |
| 2015/0245886 | A1* | 9/2015 | Hegland | A61C 5/10 433/29 |

* cited by examiner

IN-SITU DENTAL RESTORATION PROCESS AND APPARATUS

CROSS-REFERENCE TO RELATED APPLICATIONS

Not Applicable.

FIELD OF THE DISCLOSURE

This disclosure relates generally to the field of dental restoration, and more particularly to advanced in-situ dental restoration methods and apparatuses.

BACKGROUND OF THE DISCLOSURE

Typically, in-situ dental restorations are limited to preparing existing dental structure for receiving a dental prosthetic, such as an inlay, onlay, crown, bridge or veneer that is prepared outside of the subjects mouth from a dental impression of the prepared existing dental structure. The conventional process involves preparing the dental structure for a prosthetic, obtaining an impression of the existing dental structure that has been prepared for receiving a prosthetic, providing a temporary or provisional restoration, preparing a prosthetic from the impression, removing the temporary restoration, installing the prosthetic, and optionally making minor adjustments to the restored structure during the installation step. There are certain disadvantages associated with these conventional dental restoration techniques. Most notably, the subject is usually required to visit the dentist at least twice, and endure an often unsightly and sometimes uncomfortable temporary restoration for several days or even weeks.

Advanced dental restoration techniques involving only a single visit have been developed. For example, the Chairside Economical Restoration of Esthetic Ceramics (CEREC) dental restoration technique allows a dental practitioner to use three-dimensional photography, along with computer-aided design (CAD) and computer-aided manufacturing (CAM). In this technique, an optical or virtual impression of the dental structure that has been prepared for receiving a restoration is generated using a digital camera that generates image data that is subsequently processed and manipulated such as by using biogeneric comparisons to develop a three-dimensional virtual model of the restoration. The restoration can be manufactured by milling a solid block of ceramic material using diamond burs. The completed restoration is then bonded to the existing dental structure using a resin cement. The entire process can be completed in a single visit in many cases involving a simple restoration. Even relatively complex restorations can often be completed within the same day or on two consecutive days.

My U.S. Pat. No. 7,217,131 describes an in-situ dental restoration method and kit in which a dental restoration or prosthesis is formed within a subject's mouth by preparing selected dental structure for application of a restoration, fitting a mold over the teeth that are to be restored, the mold defining a space that is filled with a fluid, curable composition, curing the composition, and removing the mold to provide a restored dental structure. The disclosed process can involve preparation of a waxed-up model of a planned restoration of the existing teeth and preparation of a mold from the waxed-up model. These steps generally involve a substantial amount of hands-on manipulations by a dentist or a dental laboratory technician, and cannot typically be completed in a single visit or even on the same day.

My U.S. Pat. No. 8,366,445 describes an improved in-situ dental restoration method in which a camera is used to obtain digital images of an existing dental structure to generate a first three-dimensional digital model of existing dental structure that is modified to generate a second three-dimensional digital model of a planned structure. A dental mold is prepared corresponding to the specifications of the second digital model. The mold is fitted over the existing dental structure to be restored, and a void volume defined between the existing dental structure and the internal walls of the mold is filled with a liquid, curable composition that is subsequently cured. The mold is then removed to provide a restored dental structure. This process eliminates the need for a waxed-up model. However, the process still requires preparation of a mold, and usually involves substantial time and labor, such that the entire process cannot usually be completed in a single visit or on consecutive days.

SUMMARY OF THE INVENTION

This disclosure provides an in-situ dental restoration method that eliminates the need for a mold, eliminating time consuming labor intensive steps needed to fabricate a mold, and thereby allowing a complete dental restoration over a shorter time period, often a single visit, a single day or two successive days. This very substantially reduces the amount of discomfort and embarrassment caused to the dental restoration patient by a temporary restoration, which generally lacks esthetic perfection and often does not fit well onto the existing dental structure.

The process includes scanning an existing dental structure to generate a first three-dimensional digital model, modifying the first digital model to generate a second digital model corresponding with a planned dental structure that is different from the existing dental structure, and using an additive manufacturing process and apparatus for fabricating the planned dental structure directly on the existing dental structure.

DESCRIPTION OF THE DISCLOSED EMBODIMENTS

The methods and apparatuses disclosed herein differ significantly from previous methods and apparatuses used for dental restoration. Rather than using in-situ molding techniques or preparing dental prosthesis that conform to existing dental structure that has been prepared for receipt of the dental prosthesis in a process that necessarily requires subsequent installation and usually requires multiple sessions and a substantial time during which the dental patient is provided with a provisional restoration, the disclosed processes and apparatuses facilitate a restoration in which the artificial dental structure is formed directly on existing dental structure that has been prepared for receipt of the restoration using stereolithographic or other additive manufacturing techniques and apparatuses.

Figure 1:
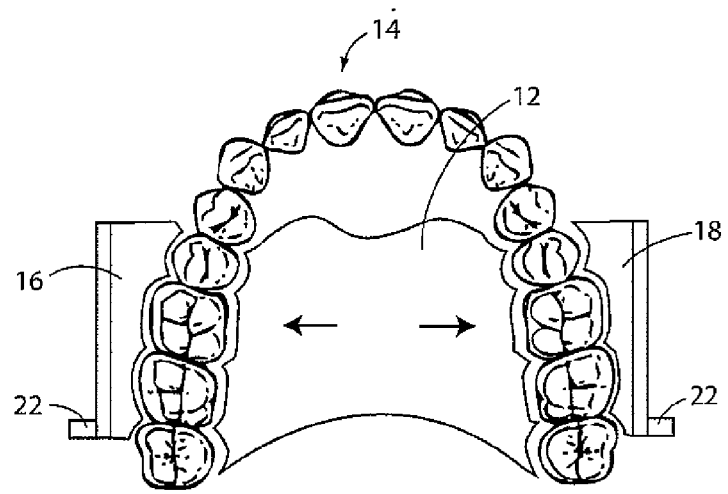
FIG. 1 is a top view of components of a fixture for maintaining the position of an additive manufacturing apparatus relative to teeth of a patient to achieve a dental restoration.
Figure 2A:
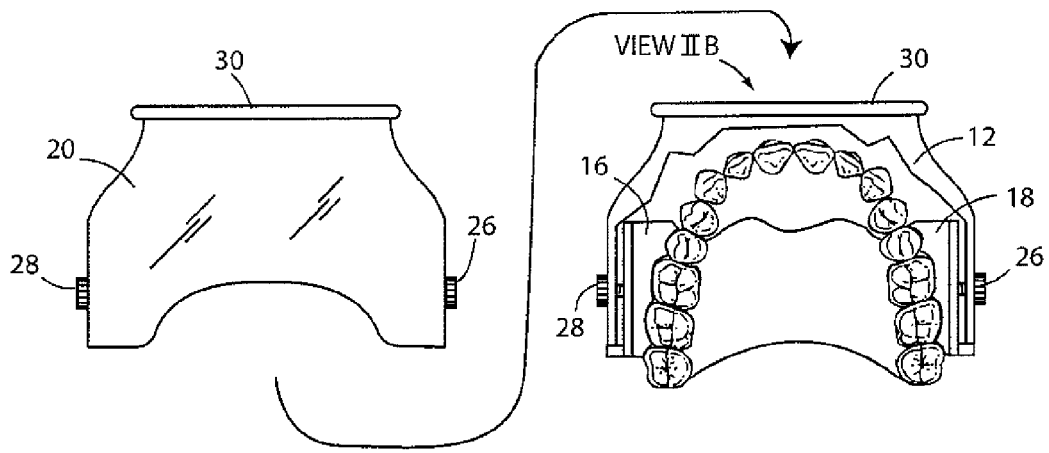
FIG. 2A is a top view showing assembly of the fixture on the teeth.
Figure 2B:
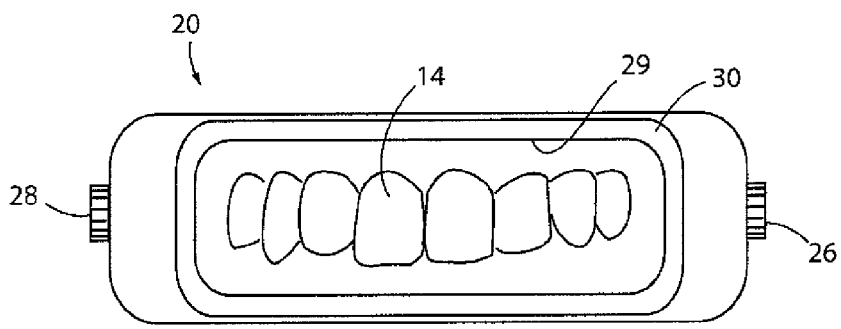
FIG. 2B is a front view of the fixture fully installed on the teeth.

In certain embodiments, the additive manufacturing apparatus is affixed to a mouth of a patient in need of dental restoration using a jig or fixture for holding an additive fabricating machine in a fixed position relative to the existing dental structure of the patient that is in need of dental restoration. An example of a fixture for holding an additive fabricating machine in a fixed position relative to a mouth of a patient is shown in FIGS. 1, 2A and 2B, The fixture includes a palate block 12 configured to engage lingual surfaces of a patient teeth 14. The palate block 12 is configured to conform very precisely to the lingual surfaces of the teeth 14 to resist rotational and linear movement with respect to the teeth when the fixture is fully installed. An adequately precise conformation of the surfaces of the palate block 12 with the lingual surfaces of the teeth 14 is one that prevents mispositioning of the tool head of an additive manufacturing machine by more than a desired or acceptable displacement relative to a desired or intended position of the tool head of the additive fabrication machine during the dental restoration process. The fixture also includes buccal blocks 16, 18 that are configured to engage buccal or facial surfaces of teeth 14. Buccal blocks 16, 18 conform very precisely to the facial surfaces of teeth 14 to resist rotation and linear movement of the buccal blocks with the teeth when the fixture is fully installed. An adequately precise conformation of the surfaces of the buccal blocks with the teeth 14 is one that prevents unacceptable movement of the tool head of an additive manufacturing machine during the dental restoration process.

The palate block 12 and buccal blocks 16, 18 can be fabricated from plastic materials (e.g., acrylic or polycarbonate plastic blocks) that are milled to the required dimensions, which can be determined using a 3-D scanner that can analyze the dimensions of the tooth surfaces and generate a 3-D digital model of the tooth surfaces that are to be engaged by the buccal and palate blocks. A 3-D digital model of the buccal and palate blocks is then generated and used in a computer-aided milling process to produce the palate block 12 and buccal blocks 16, 18.

After the palate block 12 and buccal blocks 16, 18 have been fabricated and positioned in the mouth of the patient as shown in FIG. 1, a connector 20 is used to lock the blocks 12, 16 and 18 in place, with the blocks conformingly engaged with the teeth, and with the connector 20 in a fixed position relative to blocks 12, 16 and 18 and teeth 14.

The buccal blocks 16, 18 can be provided with stops 22 on sides of the blocks opposite the sides engaging the facial surfaces of teeth 14. Stops 22, which may extend outwardly from blocks 16, 18 can be configured to engage a distal end (furthest from the lips) of the installed connector 20. Connector 20 is a hollow encasement having a distal open end that allows the connector to slide over the buccal blocks 16, 18, as illustrated in FIG. 2A. Fasteners, such as thumb screws 26, 28 can be provided to fix teeth 14, blocks 12, 16 and 18, and connector 20 in place so that there is no movement of the blocks 12, 16 and 18 or the connector 20 with respect to teeth 14.

A window 29 (shown in FIG. 2B) is defined at the proximal or labial end of connector 20 to allow a tool head (e.g., a print head) of an additive fabricating machine to build structure on existing dental structure. In the illustrated embodiment, window 29 facilitates access to the incisors, canines and each of the first molars. However, various modifications are possible that would facilitate dental restorations using additive fabrication techniques on other teeth.

Figure 3A:
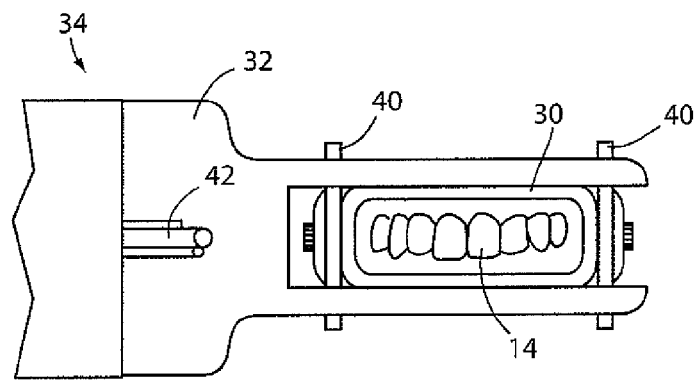
FIG. 3A is an illustration of an additive fabricating apparatus fixed in position relative to the teeth using the fixture illustrated in FIGS. 1, 2A and 2B.
Figure 3B:
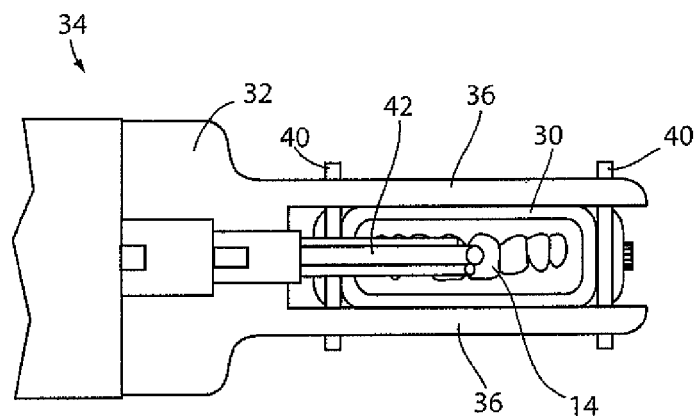
FIG. 3B is an illustration of the additive fabricating apparatus fixed in position relative to the teeth with the tool head of the additive fabricating apparatus positioned over the teeth for deposition of material to achieve the desired restoration.

In the illustrated embodiment, a flange 30 is defined at the distal end of connector 20 to facilitate positioning of a printer table 32 of an additive fabricating apparatus 34 (FIGS. 3A and 3B). The flange 30 is sized and shaped to fit exactly into grooves (not shown) provided in arms 36 that extend from printer table 32. In the illustrated embodiment, arms 36 are parallel and engage opposite edges of flange 30. Removable pins 40 can be used to firmly hold flange 30 in a fixed position relative to printer table 32 and apparatus 34. Screws, bolts, cotter pins or various other fastening means may be employed as a substitute for pins 40.

Additive fabricating apparatus 34 includes a tool head 42 (e.g., a print head) that is movable in any direction (e.g., along three mutually perpendicular axes). As illustrated in FIG. 3B, tool head 42 is positional over teeth 14 to build layers of material on the existing dental structure as needed to complete a dental restoration in accordance with a planned structure.

Figure 4:
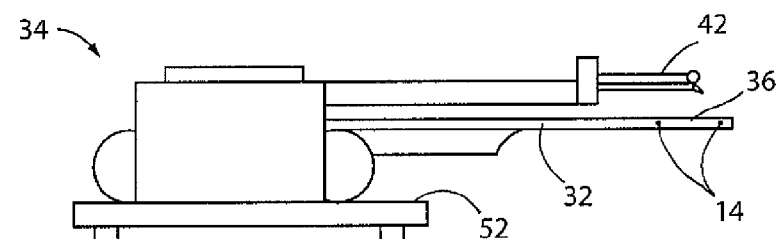
FIG. 4 shows a cart for supporting the additive fabricating apparatus during the dental restoration.
Figure 4:
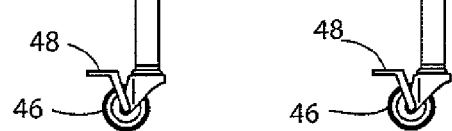
Figure 5:
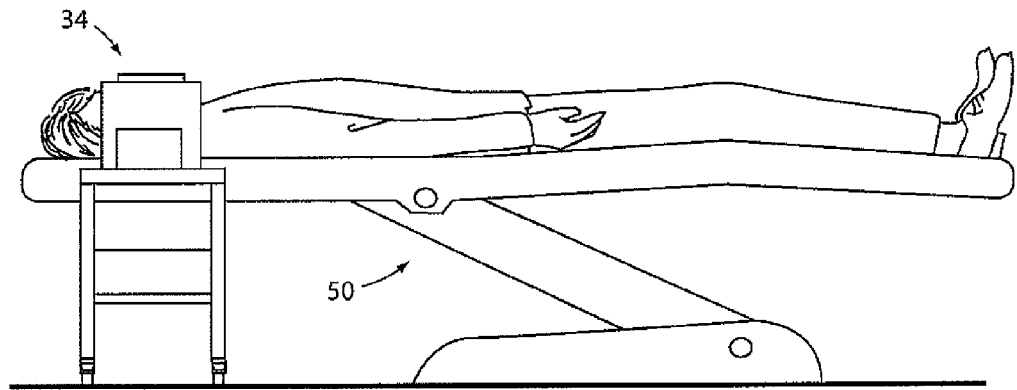
FIG. 5 is a side view of the additive fabricating apparatus and fixture fully positioned and ready for dental restoration of the teeth of a patient.
Figure 6:
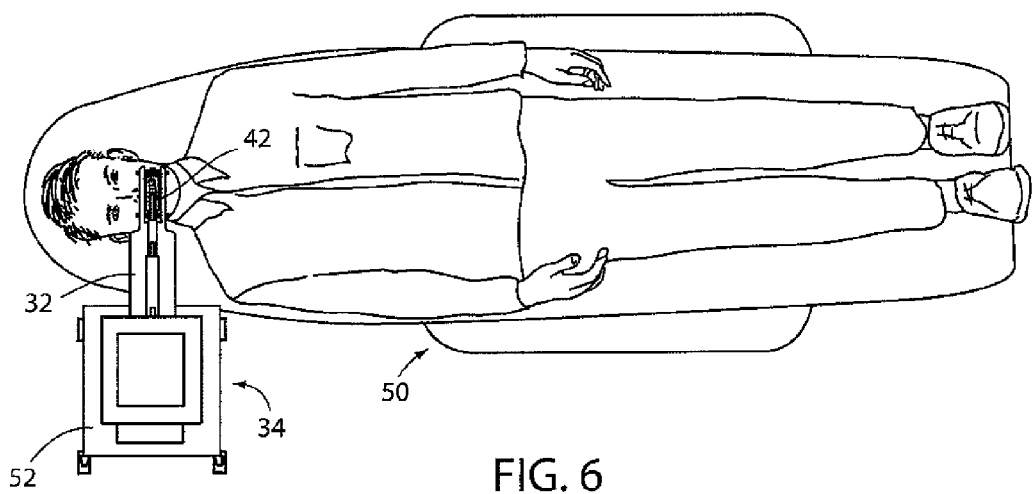
FIG. 6 is a top view of the apparatus and patient shown in FIG. 5.

As illustrated in FIG. 4, the fabricating apparatus 34 can be supported on a cart 44 that allows the fabricating apparatus to be properly positioned relative to the patient during positioning of flange 30 between arms 36 of print table 32. Cart 44 can include wheels 46 that allows the cart to be easily rolled around and repositioned as needed as the additive fabricating apparatus 34 is being fixed into position relative to connector 20 and therefore relative to teeth 14. Locks 48 can be included to lock wheels 46 in a fixed position to prevent movement of the fabricating apparatus 34 during the restoration. The illustrated apparatus 34 and cart 44 can be used with a conventional dental chair 50, as illustrated in FIGS. 5 and 6. Dental chair 50 can be extended to or near a full back position, placing the patient in a horizontal position. Chair 50 can be raised or lowered as needed to adjust the height of flange 30 equal to the height of the grooves in arms 36. Alternatively, or in addition, cart 44 can be provided with height adjustment means (not shown) for raising the support surface 52 on which the apparatus 34 is supported.

Various conventional techniques may be employed for preparing the fixture used to position the teeth of a patient relative to an apparatus 34 for additive fabricating of dental structure. For example, optical digital scanning techniques (e.g., laser scanning) can be used for determining the conformational surface structure and dimensions needed for the fixture, and computer-aided manufacturing (CAD) techniques can be employed for fabricating a customized fixture for a patient. As another alternative, the fixtures can be molded by first taking impressions that are used to fabricate a mold. While the illustrated fixture is designed to facilitate dental restorations of incisors, canines, and first premolars, fixtures can be designed to facilitate dental restorations on generally any teeth, and multiple fixtures can be prepared to provide more extensive restorations.

The apparatus 34 can be any additive manufacturing apparatus, 3-D printer, or the like used to form a solid three-dimensional object by an additive process in which successive layers are deposited or laid down in different shapes. Examples of suitable additive processes and apparatuses include stereolithographic techniques employing a photopolymer and digital light processing also employing a photopolymer. Examples of photopolymers include various commercially available acrylic based photopolymerizable compositions and the like.

Before the fixture is prepared and installed, the teeth can be prepared for the dental restoration, such as by roughening surfaces of the teeth to promote bonding.

The desired or planned dental structure can be prepared by a dental professional using a dental computer-aided design/computer-aided manufacturing system (CAD/CAM) such as disclosed in U.S. Pat. No. 8,366,445, incorporated herein by reference.

The processes and apparatus disclosed herein can be used to repair a fractured tooth, a decayed tooth, a worn tooth, a discolored tooth, a misshaped tooth or an improperly positioned tooth.

The described embodiments are preferred and/or illustrated, but are not limiting. Various modifications are considered within the purview and scope of the appended claims.

What is claimed is:

1. A process for restoring dental structure, comprising:
generating a digital model corresponding with a planned dental restoration structure; and
fabricating the planned dental restoration structure in accordance with the generated digital model directly on an existing dental structure in a mouth of a patient in need of dental restoration using an additive manufacturing process in which successive layers of material are built on the existing dental structure as needed to complete the planned dental restoration structure, wherein the additive manufacturing process is done using a three-dimensional printer.

2. A process for restoring dental structures, comprising:
generating a digital model corresponding with a planned dental restoration structure; and
fabricating the planned dental restoration structure in accordance with the generated digital model directly on an existing dental structure in a mouth of a patient in need of dental restoration using a stereolithographic technique in which successive layers of material are built on existing dental structure as needed to complete the planned dental restoration structure.

3. The process of claim 2, further comprising holding a three-dimensional printer used for the stereolithography in position relative to existing dental structure.

4. The process of claim 3, in which a fixture is attached to dental structure adjacent the planned restoration and to the three-dimensional printer to hold the three-dimensional printer in position relative to the existing dental structure.

5. The process of claim 4, in which the fixture includes a block configured to engage lingual surfaces of teeth adjacent the planned restoration, two buccal blocks that are each configured to engage opposite facial surfaces of the teeth adjacent the planned restoration, and a connector that locks the blocks together.

6. The process of claim 5, in which the connector is a hollow structure having a distal open end adapted to slide over the buccal blocks and a proximal window for additive fabrication of the planned dental structure.

7. The process of claim 6, in which the buccal blocks include stops configured to engage the connector.

8. The process of claim 5, in which the connector includes fasteners for fixing the positions of the block configured to engage lingual surfaces and buccal blocks relative to the existing dental structure.

9. The process of claim 5, in which the connector includes a flange sized and configured to be affixed to a printer table of the additive fabricating machine.

10. The process of claim 4, in which the fixture is provided with conformational surface structure to facilitate precise engagement of the fixture with surfaces of the existing dental structure.

11. The process of claim 10, in which the conformational surface structure is determined using optical digital scanning.

12. The process of claim 2, in which the digital model corresponding with the planned dental restoration structure is generated by scanning the existing dental structure to generate a first three-dimensional digital model corresponding to the existing dental structure, and modifying the first three-dimentional digital model to obtain the digital model corresponding with the planned dental restoration structure.

13. The process of claim 2, wherein the stereolithographic technique employs an acrylic based photopolymerizable composition.

* * * * *